US00PP19680P2

(12) United States Plant Patent
Klemm

(10) Patent No.: US PP19,680 P2
(45) Date of Patent: Feb. 10, 2009

(54) ***LOBELIA* PLANT NAMED 'KLELE06114'**

(50) Latin Name: *Lobelia erinus*
Varietal Denomination: KLELE06114

(75) Inventor: Nils Klemm, Stuttgart (DE)

(73) Assignee: Klemm + Sohn GmbH + Co. Kg, Stuttgart (DE)

( * ) Notice: Subject to any disclaimer, the term of this patent is extended or adjusted under 35 U.S.C. 154(b) by 0 days.

(21) Appl. No.: 12/002,471

(22) Filed: Dec. 17, 2007

(51) Int. Cl.
*A01H 5/00* (2006.01)

(52) U.S. Cl. ..... Plt./451

(58) Field of Classification Search ..... Plt./451
See application file for complete search history.

(56) References Cited

PUBLICATIONS

UPOV ROM GTITM Computer Database, GTI Jouve Retrieval Software Feb. 2008 Citation for 'KLELE06114'.*

* cited by examiner

*Primary Examiner*—Wendy C. Haas
(74) *Attorney, Agent, or Firm*—C. A. Whealy

(57) ABSTRACT

A new and distinct cultivar of *Lobelia* plant named 'KLELE06114', characterized by its semi-upright and trailing plant habit; freely branching habit and short internodes; dense and bushy plant form; continuously and freely flowering habit; and dark blue-colored flowers with white-colored eyes.

1 Drawing Sheet

Botanical designation: *Lobelia erinus.*
Cultivar denomination: 'KLEIE06114'.

BACKGROUND OF THE INVENTION

The present invention relates to a new and distinct cultivar of *Lobelia,* botanically known as *Lobelia erinus* and hereinafter referred to by the name 'KLELE06114'.

The new *Lobelia* is a product of a planned breeding program conducted by the Inventor in Stuttgart, Germany. The objective of the breeding program is to create new freely and early-flowering *Lobelia* cultivars with good branching habit and attractive flower coloration.

The new *Lobelia* originated from a cross-pollination made by the Inventor in June, 2003 of a proprietary seedling selection of *Lobelia erinus* identified as code number W 049, not patented, as the female, or seed, parent with a proprietary seedling selection of *Lobelia erinus* identified as code number 040127, not patented, as the male, or pollen, parent. The new *Lobelia* was discovered and selected by the Inventor as a single flowering plant with the progeny of the stated cross-pollination grown in a controlled environment in Stuttgart, Germany in April, 2004.

Asexual reproduction of the new cultivar by terminal cuttings in a controlled environment in Stuttgart, Germany since May, 2004, has shown that the unique features of this new *Lobelia* are stable and reproduced true to type in successive generations.

SUMMARY OF THE INVENTION

Plants of the cultivar KLELE06114 have not been observed under all possible environmental conditions. The phenotype may vary somewhat with variations in environment such as temperature and light intensity without, however, any variance in genotype.

The following traits have been repeatedly observed and are determined to be the unique characteristics of 'KLELE06114'. These characteristics in combination distinguish 'KLELE06114' as a new and distinct cultivar of *Lobelia:*

1. Semi-upright and trailing plant habit.
2. Freely branching habit and short internodes; dense and bushy plant form.
3. Continuously and freely flowering habit.
4. Dark blue-colored flowers with white-colored eyes.

Plants of the new *Lobelia* differ from plants of the female parent selection in the following characteristics:

1. Plants of the new *Lobelia* are more trailing than and not as mounding as plants of the female parent selection.
2. Plants of the new *Lobelia* and the female parent selection differ in flower color as plants of the female parent selection have lighter blue-colored flowers.

Plants of the new *Lobelia* differ from plants of the male parent selection in the following characteristics:

1. Plants of the new *Lobelia* have stronger stems than plants of the male parent selection.
2. Plants of the new *Lobelia* and the male parent selection differ in flower color as plants of the male parent selection have lighter blue-colored flowers.

Plants of the new *Lobelia* can be compared to plants of the cultivar Dark Blue Angel, not patented. In side-by-side comparisons conducted in Stuttgart, Germany, plants of the new *Lobelia* differed from plants of the cultivar Dark Blue Angel in the following characteristics:

1. Plants of the new *Lobelia* were more trailing than and not as upright as plants of the cultivar Dark Blue Angel.
2. Flowers of plants of the new *Lobelia* were darker blue in color than flowers of plants of the cultivar Dark Blue Angel.

BRIEF DESCRIPTION OF THE PHOTOGRAPH

The accompanying colored photograph illustrates the overall appearance of the new *Lobelia,* showing the colors as true as it is reasonably possible to obtain in colored reproductions of this type. Colors in the photograph may differ slightly from the color values cited in the detailed botanical description which accurately describe the colors of the new *Lobelia.* The photograph is a close-up view of typical flowers of 'KLELE06114'.

DETAILED BOTANICAL DESCRIPTION

The aforementioned photograph and following observations, measurements and values describe plants grown in Stuttgart, Germany during the spring in a glass-covered greenhouse under commercial practice with day temperatures ranging from 12° C. to 20° C., night temperatures ranging from 10° C. to 14° C. Plants were pinched one time at the time of planting. Plants had been growing for about four months when the photograph and description were taken. In the following description, color references are made to The Royal Horticultural Society Colour Chart, 2001 Edition, except where general terms of ordinary dictionary significance are used.

Botanical classification: *Lobelia erinus* cultivar KLELE06114.

Parentage:

*Female parent.*—Proprietary seedling selection of *Lobelia erinus* identified as code number W 049, not patented.

*Male parent.*—Proprietary seedling selection of *Lobelia erinus* identified as code number 040127, not patented.

Propagation:

*Type cutting.*—Terminal vegetative cuttings.

*Time to initiate roots, summer.*—About 14 days at 22° C.

*Time to initiate roots, winter.*—About 20 days at 20° C.

*Time to produce a rooted young plant, summer.*—About three weeks at 22° C.

*Time to produce a rooted young plant, winter.*—About four weeks at 20° C.

*Root description.*—Fine, fibrous.

*Rooting habit.*—Freely branching; moderately dense.

Plant description:

*Form.*—Semi-upright and trailing plant habit. Freely branching habit with lateral branches developing at potentially every node; short internodes; dense and bushy plant habit. Moderately vigorous growth habit.

*Plant height.*—About 10 cm to 15 cm.

*Plant width. About* 15 cm to 20 cm.

*Lateral branch description.*—Length: About 10 cm to 15 cm. Diameter: About 1.5 mm to 2 mm. Internode length: About 1 cm to 2.5 cm. Strength: Weak. Texture: Smooth, glabrous. Color: 137A.

Foliage description:

*Arrangement.*—Alternate, simple; sessile.

*Length, basal leaves.*—About 5 mm to 7 mm.

*Width, basal leaves.*—About 2 mm.

*Shape.*—Lanceolate.

*Apex.*—Acute.

*Base.*—Truncate.

*Margin.*—Entire.

*Texture, upper and lower surfaces.*—Smooth, glabrous.

*Venation pattern.*—Pinnate; arcuate.

*Color.*—Developing and fully expanded foliage, upper surface: 137A; venation, 137A. Developing and fully expanded foliage, lower surface: 137A; venation, 137A.

Flower description:

*Flower arrangement/shape.*—Flowers arranged singly at lateral apices. Flowers held mostly outwardly. Flowers persistent. Freely flowering with about five to eleven flowers and flower buds per lateral branch; continuously flowering with older flowers are overgrown by new flowers and foliage. Flowers not fragrant. Flowers tubular with three larger lower petals and two smaller upright petals.

*Natural flowering season.*—Plants flower continuously during the spring in Germany.

*Flower longevity on the plant.*—Longevity of individual flowers is highly dependent on weather conditions; typically about one week.

*Flower size.*—Diameter: About 1.5 cm. Depth (height): About 1.5 cm.

*Flower buds.*—Length: About 5 mm to 8 mm. Diameter: About 3 mm. Shape: Ovoid. Color: 86A.

*Petals.*—Arrangement: Single whorl of five petals, fused; three larger lower petals and two smaller upper petals. Shape: Ovate. Length: About 1 cm to 1.5 cm. Width: About 5 mm. Apex: Obtuse. Margin: Entire. Texture, upper and lower surfaces: Smooth, glabrous. Color: When opening and fully opened, upper surface: 93A; small spots on lower petals, close to 155A. When opening and fully opened, lower surface: 94B.

*Sepals.*—Arrangement: Single whorl of five sepals, fused at the base; vase-shaped calyx. Length: About 7 mm. Width: About 1 mm. Shape: Lanceolate. Apex: Acuminate. Margin: Entire. Texture, upper and lower surfaces: Smooth, glabrous. Color, upper surface: 147A. Color, lower surface: 147A overlain with 183B.

*Peduncles.*—Length: About 2 cm to 3 cm. Diameter: About 1 mm. Angle: About 30° from vertical. Strength: Weak. Texture: Smooth, glabrous. Color: 137A.

*Reproductive organs.*—Stamens: Quantity per flower: About five. Anther length: About 2 mm. Anther shape: Elliptic. Anther color: 93A. Pollen amount: Abundant. Pollen color: 12A. Pistils: Quantity per flower: One. Pistil length: About 1 cm. Stigma shape: Round. Stigma color: 79A. Style length: About 7 mm. Style color: 93A; underside, 145B. Ovary color: 145A.

*Fruits.*—Length: About 4 mm. Diameter: About 2 mm. Texture: Rugose. Color: 165B.

*Seeds.*—Length: Less than 0.2 mm. Diameter: Less than 0.2 mm. Color: 166A.

Disease/pest resistance: Plants of the new *Lobelia* have not been noted to be resistant to pathogens and pests common to *Lobelia.*

Temperature tolerance: Plants of the new *Lobelia* have been observed to tolerate temperatures from about 1° C. to about 32° C.

It is claimed:

1. A new and distinct *Lobelia* plant named 'KLELE06114' as illustrated and described.

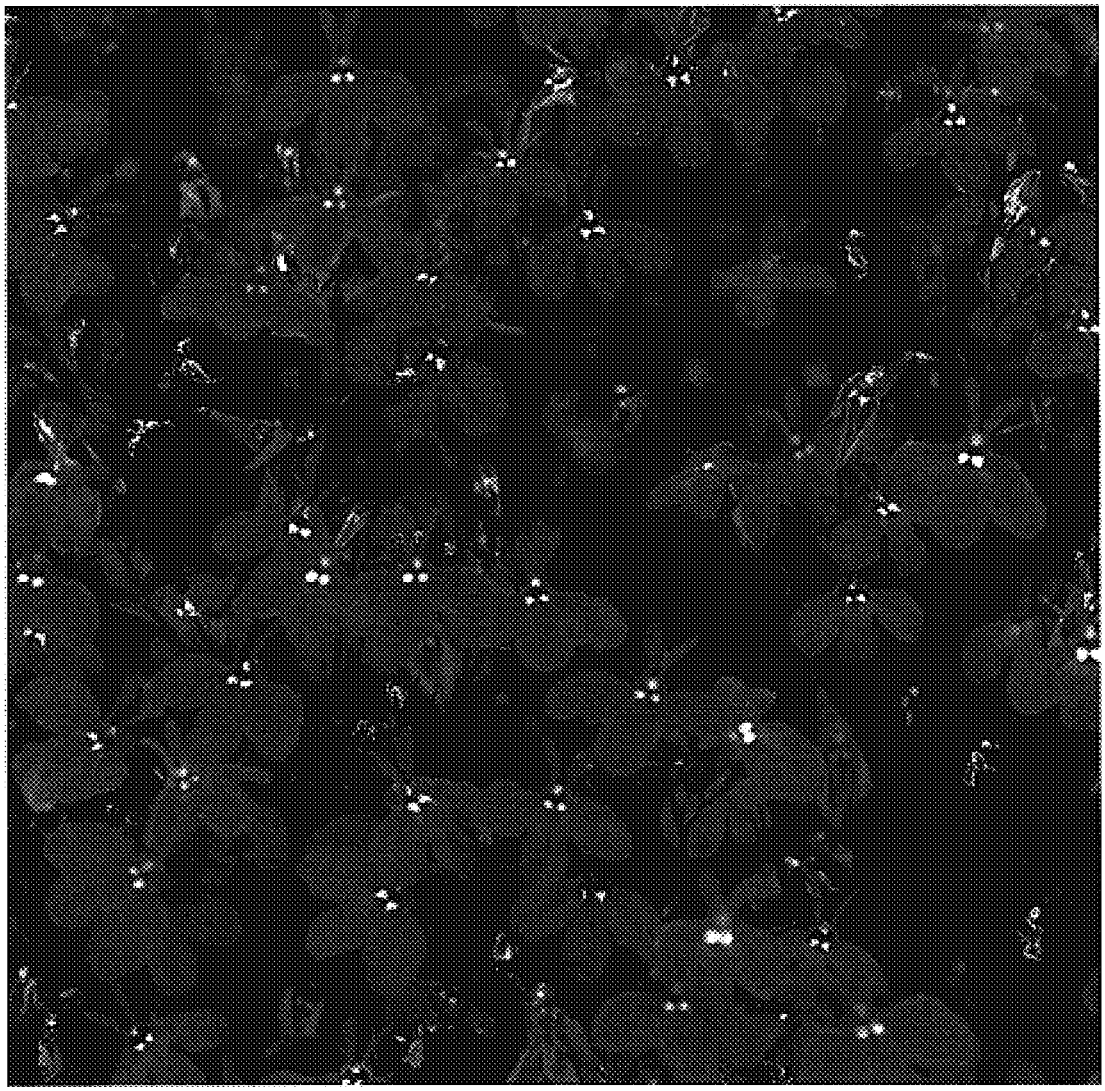

* * * * *